United States Patent [19]
Pandey et al.

[11] Patent Number: 5,952,366
[45] Date of Patent: Sep. 14, 1999

[54] ALKYL ETHER ANALOGS OF CHLORINS HAVING AN N-SUBSTITUTED IMIDE RING

[75] Inventors: Ravindra K. Pandey, Williamsville; William R. Potter; Thomas J. Dougherty, both of Grand Island, all of N.Y.

[73] Assignee: Health Research, Inc., Buffalo, N.Y.

[21] Appl. No.: 09/102,394

[22] Filed: Jun. 22, 1998

Related U.S. Application Data

[63] Continuation-in-part of application No. 08/812,029, Mar. 6, 1997, Pat. No. 5,864,035, which is a continuation-in-part of application No. 08/613,134, Mar. 8, 1996, Pat. No. 5,770,730.

[51] Int. Cl.$^6$ .................. C07D 487/22; A61K 31/40
[52] U.S. Cl. .................. 514/410; 540/472; 540/145
[58] Field of Search .................. 540/145; 514/410

[56] References Cited

U.S. PATENT DOCUMENTS

| 5,459,159 | 10/1995 | Pandey et al. | 514/410 |
| 5,591,847 | 1/1997 | Pandey et al. | 540/472 |
| 5,770,730 | 6/1998 | Pandey et al. | 540/472 |

OTHER PUBLICATIONS

Lee et al., J. Chem. Soc. Perkin Trans. 1. 1993, 2369–77.
Fieser and Fieser, Reagents for Org. Syn, vol. 1, 1967, p. 233, John Wiley and Sons, Inc., New York.
Sripada et al. J. Lipid. Res., vol. 28, 1987, pp. 710–718.
Chang, C. et al., Differentiation of Bacteriochlorin and Isobacteriochlorin Formation by Metallation. High Yield Synthesis of Porphyrindiones via OsO$_4$ Oxidation, J. Chem. Soc., Chem. Commun., pp. 1213–1215 (1986).
Beem, E. et al., Photosensitizing Properties of Bacteriochlorophyllin α and Bacteriochlorin α, Two Derivatives of Bacterchlorophyll α, Photochemistry and Photobiology, vol. 46, No. 5, pp. 639–643 (1987).

(List continued on next page.)

Primary Examiner—Mukund J. Shah
Assistant Examiner—Pavanaram K Sripada
Attorney, Agent, or Firm—Michael L. Dunn

[57] ABSTRACT

Compounds having the generic formula:

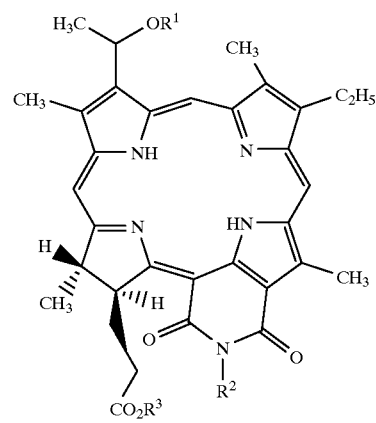

where $R^1$, $R^2$ and $R^3$ are independently alkyl of 3 through about 10 carbon atoms; provided that, $R^1$ and $R^2$ together contain at least six carbon atoms. The compounds have utility in photodynamic therapy in treatment of tumors and other diseases. The invention includes a method of treatment by contacting a tumor with the compound and then exposing the tumor to light.

9 Claims, 2 Drawing Sheets

OTHER PUBLICATIONS

Dougherty, et al., Photoradiation Therapy. II. Cure of Animal Tumors With Hematoporphyrin and Light, Journal of the National Cancer Institute, vol. 55, No. 1, pp. 115–119 (1975).

Evensen, J. et al., Photodynamic Therapy of C3H Mouse Mammary Carcinoma with Haematoporphyrin di–ethers as Sensitizers, Br. J. Cancer, 55, pp. 483–486 (1987).

Diamond, I. et al., Photodynamic Therapy of Malignant Tumors, The Lancet, pp. 1175–1177 (1972).

Lipson, R. et al., The Use of a Derivative of Hematoporphyrin in Tumor Detection, Journal of the National Cancer Institute, vol. 26, No. 1, pp. 1–10 (1961).

Pandey R. et al., Substituent Effects in Tetrapyrrole Subunit Reactivity and Pinacol–Penacolone Rearrangements :VIC–Dihydroxychlorins and VIC–Dihydroxybacteriochlorins, Tetrahedron Letters, vol. 33, No. 51, pp. 7815–7818 (1992).

Hoober, K. et al., Photodynamic Sensitizers from Chlorophyll :Purpurin–18 and Chlorin $p_6$, Photochemistry and Photobiology, vol. 48, No. 5, pp. 579–582 (1988).

Pandey, R. et al., Structure/Activity Relationships Among Photosensitizers Related to Pheophorbides and Bacteriophophorbides, Bioorganic & Medical Chemistry Letters, vol. 2, No. 5, pp. 491–496 (1992).

Pandy R. et al., Chemistry of Photofrin II and Some New Photosensitizers, SPIE vol. 1065 Photodynamic Therapy: Mechanisms, pp. 164–174 (1989).

Pandey et al., Fast Atom Bombardment Mass Spectral Analysis of Photofrin II® and its Synthetic Analogs, Biomedical and Environmental Mass Spectrometry, vol. 19, pp. 405–414 (1990).

ALKYL ETHER ANALOGS OF CHLORINS HAVING AN N-SUBSTITUTED IMIDE RING

This is a Continuation-in-Part of U.S. patent application Ser. No. 08/812,029 filed Mar. 6, 1997, now U.S. Pat. No. 5,864,035, which is a Continuation-in-Part of U.S. patent application Ser. No. 08/613,134 filed Mar. 8, 1996, granted as U.S. Pat. No. 5,770,730 on Jun. 23, 1998.

BACKGROUND OF THE INVENTION

Some porphyrins and related tetrapyrrolic compounds, e.g. chlorins and bacteriochlorins, tend to be retained in malignant tumors in higher concentrations than in normal tissues. When the tetrapyrrolic compound is exposed to light of an appropriate wavelength, an excited state may occur and a singlet oxygen atom may be released. Such compounds which become excited by light are referred to herein as photodynamic compounds. When a patient is injected with an appropriate dose of a photodynamic compound, as previously described, the compound will concentrate in tumors which are present. The tumor may then be exposed to the appropriate wavelength of light to activate the compound which results in a tumoricidal effect. The release of singlet oxygen may be the cytotoxic species which, along with various other oxygen containing radicals, kills the tumor.

Porphyrins, chlorins, and bacteriochlorins including their analogs and derivatives have therefore recently found superior utility as photodynamic compounds for use in diagnosis and treatment of disease, especially certain cancers. These compounds have also found utility in treatment of psoriasis and papillomatosis.

Photofrin® (a porphyrin derivative), has been studied in most detail and is currently being used all over the world for treatment of various types of cancers. Despite the fact that it has already been approved for commercialization in Canada, Japan, and the United States, Photofrin photosensitizing agent has some disadvantages. In particular, it both photosensitizes the skin and lacks rapid normal tissue clearance, so patients must avoid exposure to sunlight for an extended period after its use. Further, it is a complex mixture of ether and ester linked dimers and higher oligomers, making it difficult to study mechanistically.

Photofrin photosensitizing agent also absorbs at a short wavelength making deep tissue penetration difficult and sometimes not possible. It is well established that both absorption and scattering of light by tissue increases as the wavelength decreases, and the most efficient photosensitizers are those which have strong absorption bands at the red end of the visible spectrum and the near IR region. Heme proteins accounts for most of the absorption of light in the visible region. Since this drops off rapidly beyond 550 nm, the effective depth of penetration doubles from 550 to 630 nm (where Photofrin® is activated) and doubles again in going to 700 nm, followed by 10% increase in penetration by moving into the near IR region (800 nm). However, further red shift is neither desirable (because of the lack of benefit from deeper penetration) nor easily achievable. Another reason to set the ideal wavelength in the range of 700–800 nm is due to the availability of diode lasers. Advantages of diode lasers are the low cost, negligible running cost, high reliability, small size and portability. Besides these considerations, tumor localization, dark toxicity, phototoxicity, stability and formulation are also among the basic criteria to be considered for developing an efficient photosensitizer.

There is therefore still a quest for additional and new compounds for use in the field which have lower phototoxicity, better tissue clearance, better effectiveness and which absorb at higher wave lengths for better penetration.

BRIEF DESCRIPTION OF THE INVENTION

In accordance with the invention, a new series of compounds is therefore provided, which have good antitumor activity and which absorb at relatively long wave lengths of light.

More particularly, the compounds have the generic formula:

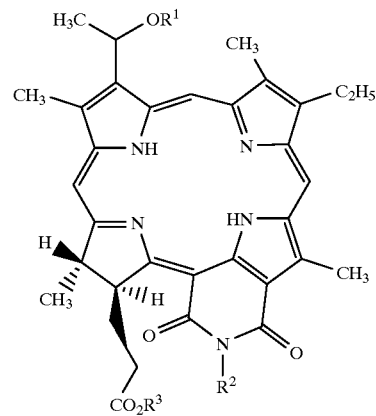

Where $R^1$, $R^2$, and $R^3$ are independently alkyl of 3 through about 10 carbon atoms; provided that, $R^1$ and $R^2$ together contain at least six carbon atoms. $R^3$ is preferably methyl or ethyl and $R^2$ and $R^3$ are preferably alkyl of 3 through 8 carbon atoms.

DETAILED DESCRIPTION OF THE INVENTION

In accordance with the invention, a compound is provided having the generic structure described above.

Among the alkyl ether derivatives of pyropheophorbide-a, it has been shown that the biological activity increased by increasing the length of the carbon chain, being maximum with n-hexyl and n-heptyl analogs, further increase in the length of carbon chain reduced the in vivo efficacy.

In order to find the effect of such substituents in other series of compounds, in accordance with the invention, a series of various alkyl ether analogs of chlorins with N-substituted cyclic imides (purpurin-18 imides) were prepared. These compounds have long wavelength absorption at 705 nm, and offer considerable latitude in testing the modeling methods as well as refining it since they offer the possibility of two sites for alkyl substitution ($R^1$ and $R^2$) and allow the log P value to be held constant while changing the size and shape of the molecules. For example, the calculated (PALLAS) log P for chlorin where $R^1$=propyl and $R^2$=decyl and vice versa and where $R^1$=heptyl and $R^2$=hexyl and vice versa are identical (10.72) (i.e. each with 11 methylene groups and 2 terminal methyl groups). Numerous other examples are obvious. Thus, we can hold constant or vary log P while changing size and steric factors as well.

Figure 1:
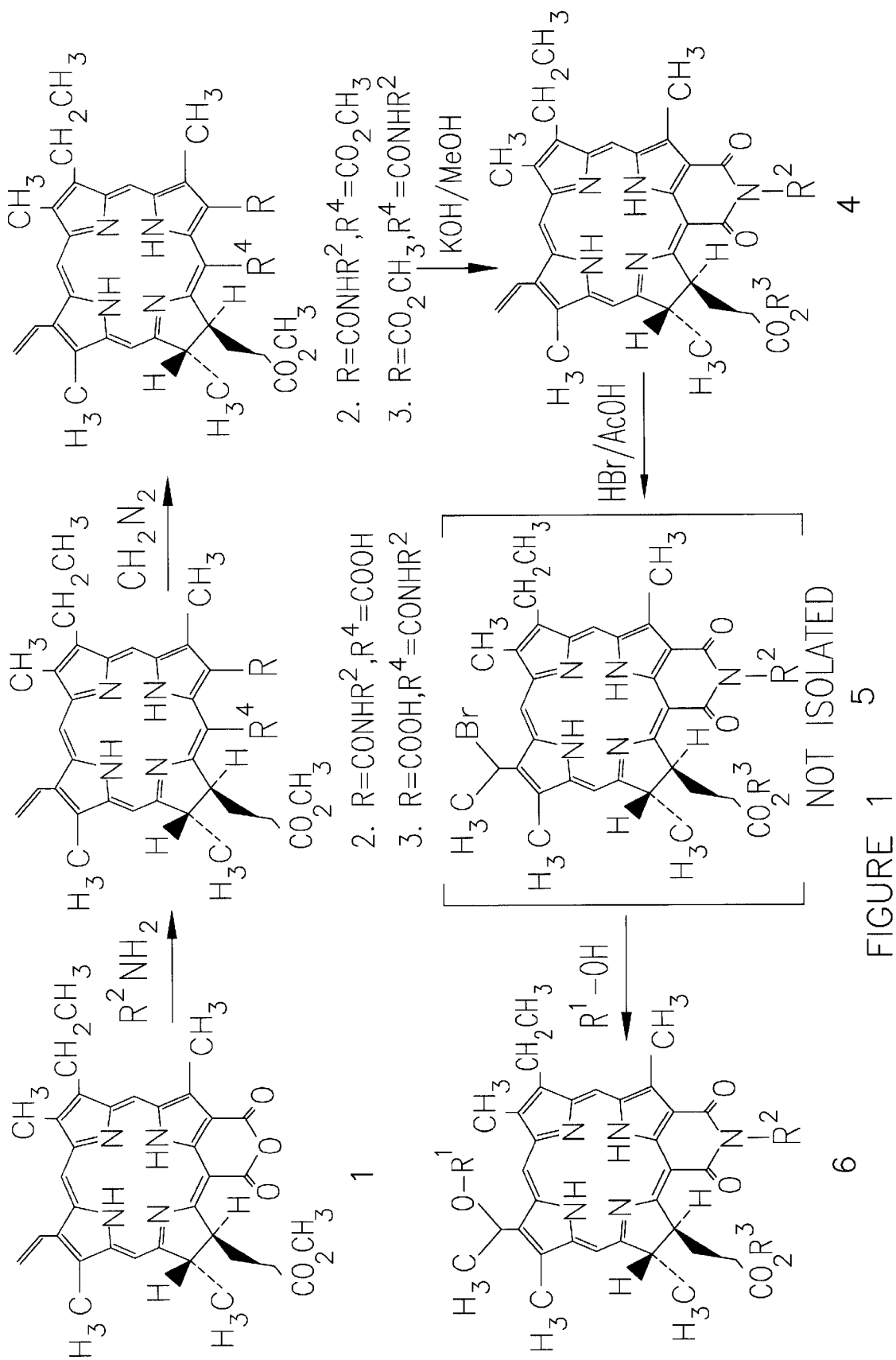
FIG. 1 is a schematic equation showing a method for preparation of compounds of the invention.
Figure 2:
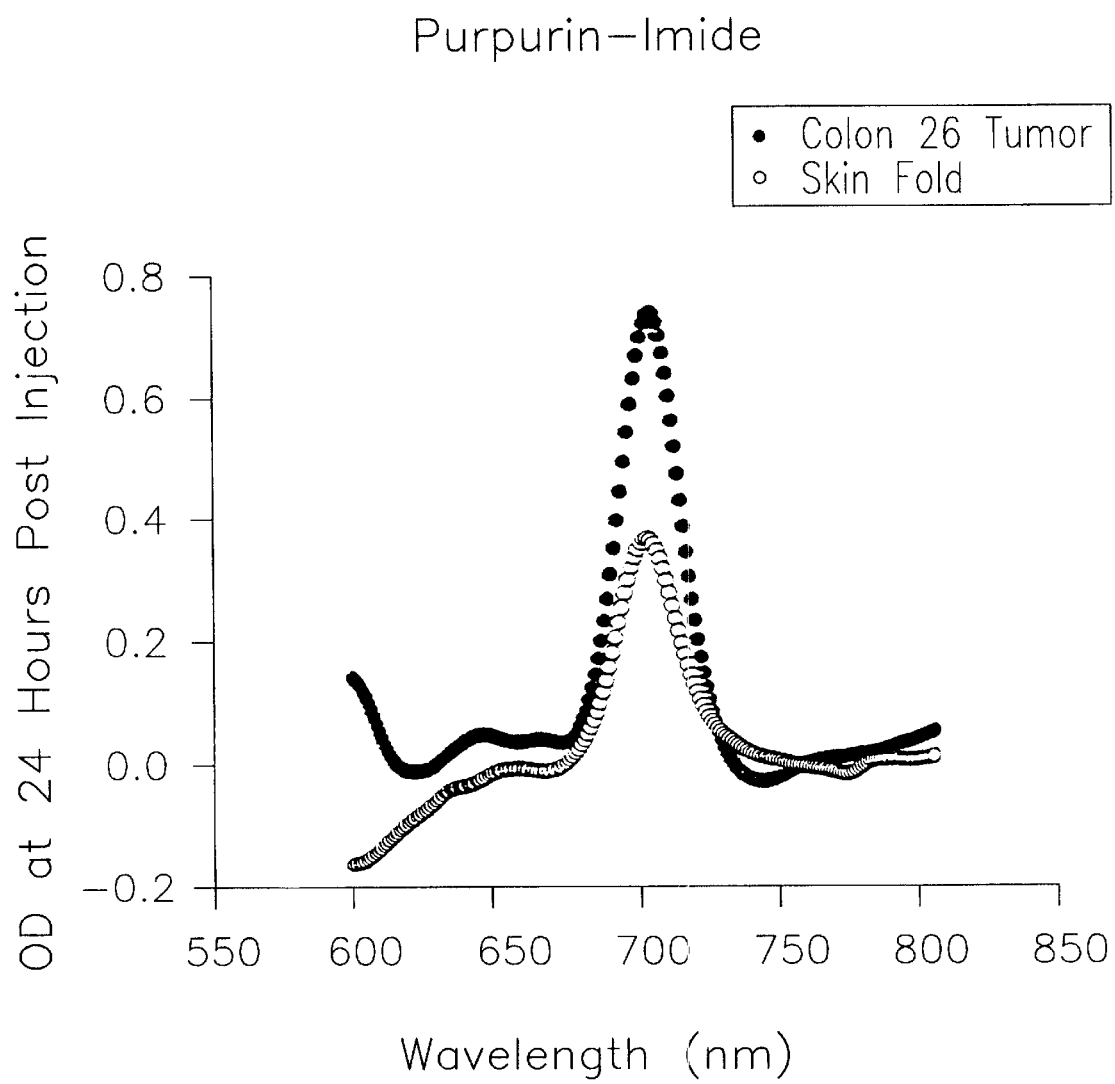
FIG. 2 is a curve showing uptake in tumor versus skin fold of a purpurinimide of the invention where $R^1$ is heptyl, $R^2$ is hexyl and $R^3$ is methyl. The uptake is measured by optical density at the desired wavelength at 24 hours post injection.

A method for preparation of the compounds of the invention is shown in the schematic equations set out in FIG. 1.

$R^1$ is alkyl of 3 through about 10 and preferably 3 to 8 carbon atoms. $R^2$ is alkyl of 3 through about 10 carbon atoms and preferably 3 to 8 carbon atoms. $R^3$ is methyl or ethyl. $R^1$ and $R^2$ together contain at least 6 carbon atoms. The alkyl groups may be linear or branded chain and may be substituted with other groups, e.g., alkoxy, halogen, ester or aromatic substituents.

Methylpheophorbide-a was isolated from the alga *Spirulina Pacifica*, and reacted with alkyl amines. The intermediate amides as carboxylic acid analogs were converted to the corresponding methyl esters, which on stirring with methanolic KOH at room temperature (5–10 min) produced the N-alkyl imide derivatives in 65–70% yield. The vinyl groups were then converted to various alkyl ether analogs by first reacting with 30% HBr/AcOH, and then with the desired alcohol (for example 4 to 6, FIG. 1). The desired compounds (Table 1) were prepared in high yield (70–75%). The methyl ester group (e.g., heptyl ether analog of N-hexyl purpurin imide 4) can be hydrolyzed to the corresponding carboxylic acid.

Various compounds of the present invention were compared for in vivo tumor response, as shown in Table 1.

Radiation induced fibrosarcoma (RIF) tumors, were implanted subcutanaceously into the axilla of 5–7 week old female C3H mice. When tumors grew to about 5 mm in diameter, the mice were injected with various doses of the photosensitizers. The mice (6 mice per group) were restrained in aluminum holders and each tumor illuminated with 135 $J/cm^2$ of light from a laser tuned at the longest wavelength absorption maximum of the photosensitizers at 705 nm. The percentage of short term control was recorded daily.

The results are set forth in Table 1. The data indicated that: (1) the hydrophobicity of the molecule can be varied by changing the length of the carbon chain (N-alkyl or -alkyl substituents), (ii) in some cases, compounds with same hydrophobic characteristics (same log p values), did not show similar activity. (iii) thus besides hydrophobicity, the steric and electronic factors also play important role in designing effective photosensitizers.

In this series, the heptyl ether derivative of purpurin imide bearing N-hexyl substituent was found to be most effective at a dose of 1.0 $\mu$mol/kg.

TABLE 1

Preliminary in vivo Activity of Alkyl Ether Analogs of Purpurin-18 imides

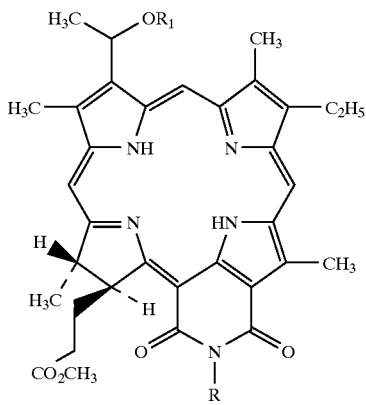

| | | Partition Coefficient | Tumor Response (%) [days]* | | | | | |
|---|---|---|---|---|---|---|---|---|
| $R^1$ | $R^2$ | (log P) | 1–2 | 7 | 14 | 21 | 30 | 90 |
| Methyl | Propyl | 6.22 | | | NR | | | |
| Propyl | Propyl | 7.22 | 100 | 33 | 17 | ongoing | | |
| Methyl | Hexyl | 7.72 | | | NR | | | |
| Propyl | Hexyl (0.5 $\mu$mol)* | 8.72 | | | NR | | | |
| Hexyl | Propyl (0.5 $\mu$mol)* | 8.72 | 100 | 66 | 33 | 17 | 17 | 17 |
| Hexyl | Propyl | 8.72 | 100 | 83 | 83 | 50 | 33 | 33 |
| Heptyl | Hexyl (0.25 $\mu$mol)* | 10.72 | 100 | 60 | 20 | 20 | 20 | 20 |
| Heptyl | Hexyl | 10.72 | 100 | 100 | 100 | 100 | 100 | 83 |

TABLE 1-continued

Preliminary in vivo Activity of Alkyl Ether Analogs of Purpurin-18 imides

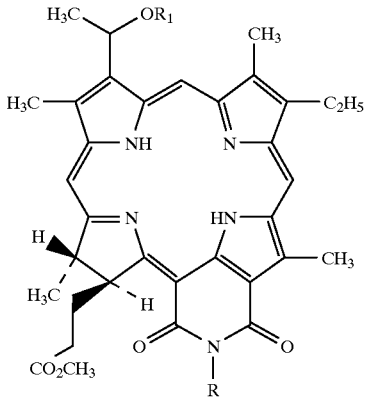

| | | Partition Coefficient | Tumor Response (%) [days]* | | | | | |
|---|---|---|---|---|---|---|---|---|
| $R^1$ | $R^2$ | (log P) | 1–2 | 7 | 14 | 21 | 30 | 90 |

*Six mice/group (RIF tumor). 1.0 μmol/kg. 705 nm, 135J/cm² (24 h post injection).

What is claimed is:

1. A compound of the formula:

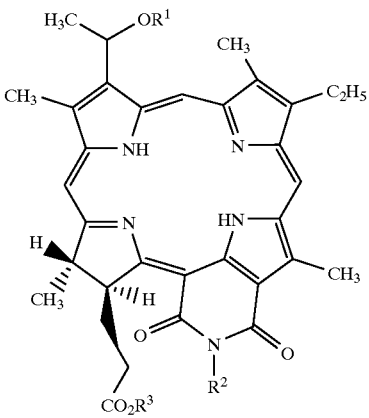

Where $R^1$, $R^2$ and $R^3$ are independently alkyl of 3 through about 10 carbon atoms; provided that, $R^1$ and $R^2$ together contain at least 6 carbon atoms.

2. The compound of claim 1 wherein $R^1$ and $R^2$ are alkyl of 3 through 8 carbon atoms and $R^3$ is methyl or ethyl.

3. The compound of claim 1 wherein $R^1$ is heptyl, $R^2$ is hexyl and $R^3$ is methyl.

4. A method for the treatment of a tumor which comprises contacting it with a compound of claim 1 and exposing it to light having a wavelength of from about 650 to about 750 nm.

5. A method for the treatment of a tumor which comprises contacting it with a compound of claim 2 and exposing it to light having a wavelength of from about 650 to about 750 nm.

6. A method for the treatment of a tumor which comprises contacting it with a compound of claim 3 and exposing it to light having a wavelength of from about 650 to about 750 nm.

7. The method of claim 4 wherein the light has a wavelength of from about 695 to about 710 nm.

8. The method of claim 5 wherein the light has a wavelength of from about 695 to about 710 nm.

9. The method of claim 6 wherein the light has a wavelength of from about 695 to about 710 nm.

* * * * *

UNITED STATES PATENT AND TRADEMARK OFFICE
CERTIFICATE OF CORRECTION

PATENT NO. : 5,952,366
DATED : September 14, 1999
INVENTOR(S) : Pandey et al.

It is certified that error appears in the above-identified patent and that said Letters Patent is hereby corrected as shown below:

Column 1,
Line 3, insert: -- This invention was made with United States government support under Grant PO1 CA55791 from the NIH. The United States government may have certain rights in this invention. --

Signed and Sealed this

Fifteenth Day of April, 2003

JAMES E. ROGAN
*Director of the United States Patent and Trademark Office*